United States Patent [19]
Carroll

[11] Patent Number: 5,961,458
[45] Date of Patent: Oct. 5, 1999

[54] MINIMALLY INVASIVE SURGICAL PROBE FOR TISSUE IDENTIFICATION AND RETRIEVAL AND METHOD OF USE

[75] Inventor: Robert G. Carroll, Largo, Fla.

[73] Assignee: Carewise Medical Products Corporation, Morgan Hill, Calif.

[21] Appl. No.: 08/972,598

[22] Filed: Nov. 18, 1997

[51] Int. Cl.$^6$ ........................................................ A61B 6/00
[52] U.S. Cl. ........................ 600/436; 600/431; 600/562; 607/96; 606/186; 604/27; 604/28; 604/35; 250/336.1; 250/363.1; 250/370.11
[58] Field of Search ................... 600/431, 436, 600/562, 567; 604/19, 20, 22, 27, 28, 35; 607/96; 606/167, 185, 186; 250/336.1, 363.01, 363.1, 362, 370.01, 370.11–370.12

[56] References Cited

U.S. PATENT DOCUMENTS

| | | | |
|---|---|---|---|
| 4,781,198 | 11/1988 | Kanabrocki | 600/431 |
| 4,801,803 | 1/1989 | Denen et al. | |
| 4,959,547 | 9/1990 | Carroll et al. | |
| 4,995,396 | 2/1991 | Inaba et al. | |
| 5,014,708 | 5/1991 | Hayashi et al. | |
| 5,036,210 | 7/1991 | Goodman | |
| 5,119,818 | 6/1992 | Carroll et al. | 600/436 |
| 5,170,055 | 12/1992 | Carroll et al. | |
| 5,762,613 | 6/1998 | Sutton et al. | 600/564 |
| 5,811,814 | 9/1998 | Leone et al. | 600/436 |
| 5,843,017 | 12/1998 | Yoon | 604/22 |
| 5,846,513 | 12/1998 | Carroll et al. | 600/436 |

FOREIGN PATENT DOCUMENTS

WO 94/03108  2/1994  WIPO .

*Primary Examiner*—Ruth S. Smith
*Attorney, Agent, or Firm*—Ceasar, Rivise, Berstein, Cohen & Pokotilow, Ltd.

[57] ABSTRACT

A probe for detecting and removing radioactively tagged tissue, e.g., a sentinel lymph node, within the body of a living being. The probe is arranged to be inserted through a small percutaneous portal into the patient's body and is movable to various positions adjacent the tagged tissue to detect the presence of radiation therefrom so that the probe can be positioned immediately adjacent that tissue to ensnare or trap it. The probe can then be removed from the being's body, carrying the tagged tissue with it. The probe may be constructed to make use of a scintillation crystal, a collimator, adjustable or fixed, and a backshielding light-pipe.

65 Claims, 2 Drawing Sheets

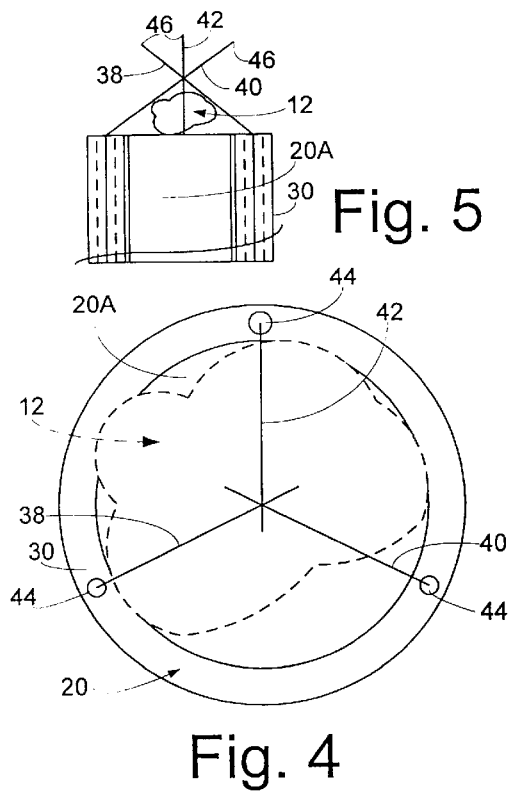
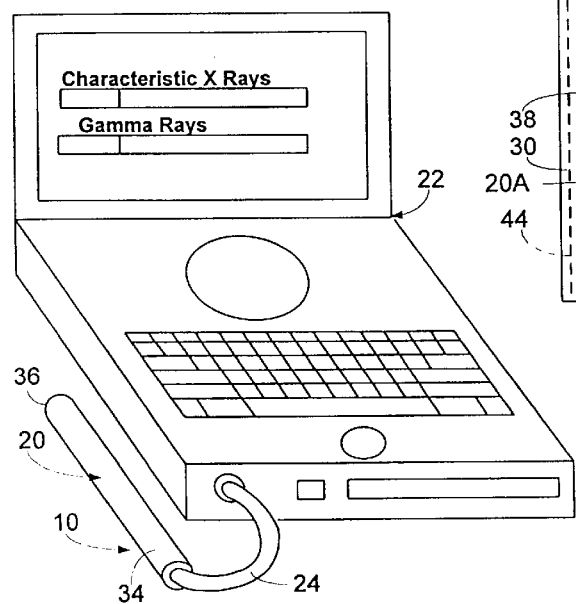
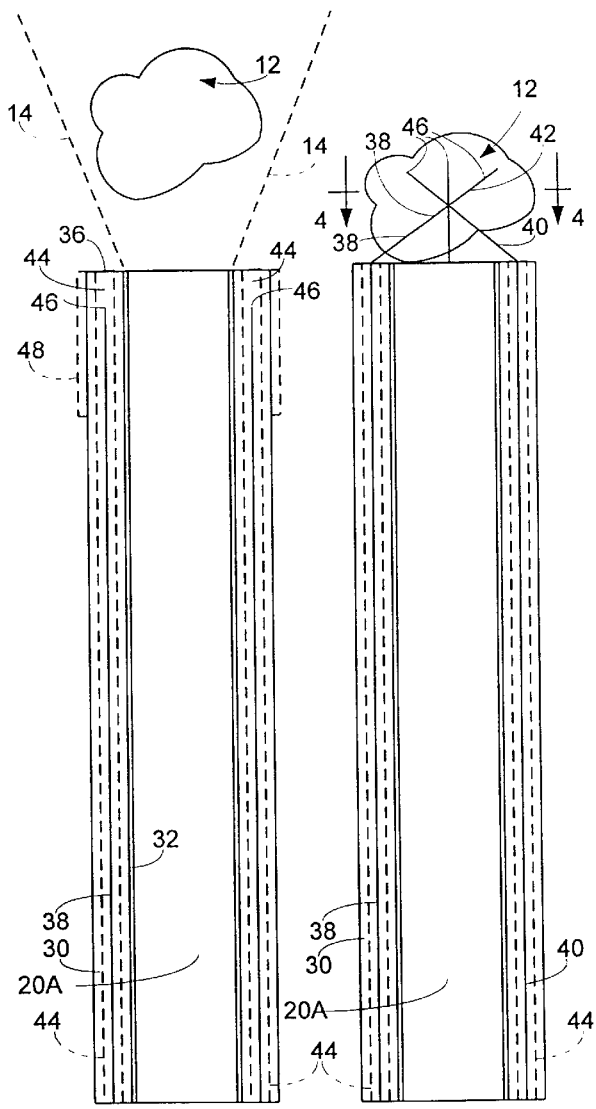
Fig. 5
Fig. 4
Fig. 2   Fig. 3
Fig. 1

MINIMALLY INVASIVE SURGICAL PROBE FOR TISSUE IDENTIFICATION AND RETRIEVAL AND METHOD OF USE

BACKGROUND OF THE INVENTION

This invention relates generally to medical devices and methods of detection and treatment of cancer, and more particularly to minimally invasive medical systems including a radiation detecting probe for locating radioactively tagged tissue, e.g., a "sentinel" lymph node, within the body of the patient and for retrieving or removing that tissue.

The use of radioactive materials to tag tissue within a patient for effecting its localization and demarcation by radiation detecting devices has been disclosed in the medical literature for at least forty years. Significant developments in the localization and demarcation of tissue bearing radioactive isotope tags for diagnostic and/or therapeutic purposes have occurred since that time. In fact, it is now becoming an established modality in the diagnosis and/or treatment of certain diseases, e.g., cancer, to introduce monoclonal antibodies or other tumor or lymph node localizing agents tagged with a radioactive isotope (e.g., Technetium 99 m, Indium 111, Iodine 123, and Iodine 125) into the body of the patient. Such radiopharmaceuticals tend to localize in particular tissue, such as the cancerous tissue, so that the gamma radiation emitted by the isotope agent can be detected by a radiation detector, e.g., a probe. In particular, the radiation detector or probe is disposed or positioned adjacent portion of the patient's body where the cancerous tissue is suspected to be in order to detect if any radiation is emanating from that site. If it is this indicates that cancerous tissue is likely to be found at that site.

Prior art, hand-held, radiation detecting probes particularly suitable for such cancer-finding applications are commercially available from the assignee of this invention, CareWise Medical Products, Inc. under the trademark C-TRAK. In U.S. Pat. Nos. 4,959,547 and 5,036,201 assigned to the same assignee as this invention there are disclosed hand-held radiation detecting probes having collimating means to establish the field of view or "solid angle of acceptance" of the probe. In U.S. Pat. Nos. 5,119,818 and 5,170,055, also assigned to the same assignee as this invention, there are disclosed hand-held radiation detecting probes and accessories optimized to biopsy radio-labeled tissues. In U.S. Pat. No. 4,801,803 (Denen et al.) there is also disclosed a hand-held radiation detecting probe.

In the diagnosis and treatment of breast cancer and prostate cancer a radiopharmaceutical can injected adjacent a detected tumor site, e.g., within the breast, to migrate to the closest draining lymph node (the "sentinel" node) so that localization of that node and its examination can be readily effected in order to evaluate the extent, if any, of metastasis of the cancer. Heretofore, no minimally invasive instrument, e.g., radioactivity detection probe, has existed to not only detect or localize the radioactively tagged tissue, e.g., the sentinel node, but also to engage or otherwise ensnare or trap it so that it can be removed for analysis.

It is a general object of this invention to provide a minimally invasive surgical probe and method of use which overcomes the disadvantages of the prior art.

SUMMARY OF THE INVENTION

These and other objects of the subject invention are achieved by providing a probe for minimally invasive introduction within the body of a living being. The probe is arranged to detect radiation emanating from radioactively tagged tissue, e.g., a sentinel lymph node, within the being's body to determine the location of that tissue. The probe is arranged to be readily manipulated and moved adjacent to the radioactively tagged tissue, and includes means (e.g., plural extendable members) for engaging (e.g., piercing and ensnaring) the radioactively tagged tissue to remove it from the being's body.

DESCRIPTION OF THE DRAWING

Other objects and many attendant features of this invention will become readily appreciated as the same becomes better understood by reference to the following detailed description when considered in connection with the accompanying drawing wherein:

FIG. 1 is an isometric view of a system including the probe assembly of the subject invention;

FIG. 2 is an enlarged longitudinal sectional view of one embodiment of the probe assembly of this invention shown located adjacent radioactively tagged tissue, e.g., a sentinel lymph node, to determine its location so that the probe assembly can be moved to a position wherein a portion of it is located immediately adjacent that tissue;

FIG. 3 is a view, similar to FIG. 2, but showing the probe assembly after it has be moved to a location immediately adjacent the tagged tissue and after its holding means has ensnared, e.g, pierced and trapped, that tissue;

FIG. 4 is an enlarged sectional view taken along line 4—4 of FIG. 3;

FIG. 5 is a view similar to FIG. 3, but showing only the distal end of the probe assembly, and wherein the tagged tissue, e.g., lymph node, is too small to be pierced by the holding means, but is nevertheless still snared or entrapped thereby;

DETAILED DESCRIPTION OF THE PREFERRED EMBODIMENTS

Figure 8:
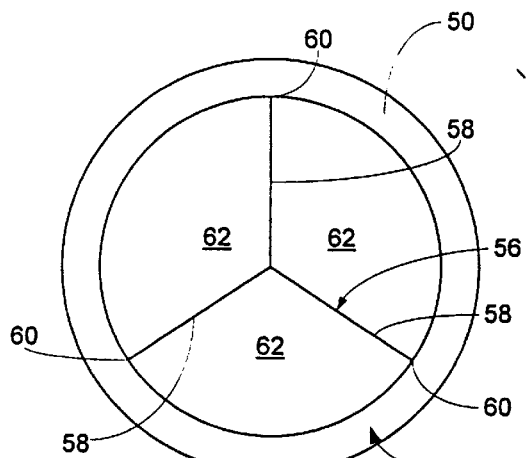
FIG. 8 is an end view of the divided single-hole collimator shown in its undivided state.

Referring now to the drawing where like reference numerals refer to like parts there is shown at 10 in FIGS. 1 a system incorporating a probe assembly 20 constructed in accordance with this invention. The system 10 is preferably constructed and arranged in accordance with the teachings of copending U.S. patent application, Ser. No. 08/430,589, filed on Apr. 25, 1995, entitled Apparatus and Methods For Determining Spatial Coordinates of Radiolabelled Tissue Using Gamma Rays And Associated Characteristic X-Rays, now U.S. Pat. No. 5,694,933, which is assigned to the same assignee as this invention and whose disclosure is incorporated by reference herein. The system is arranged to be used with any suitable radiopharmaceutical which is injected or otherwise introduced into the body of the being to be treated for specific uptake by the suspected cancer tissue or sentinel lymph node so that the probe assembly 20 of the system can determine the location of that cancer or lymph node and remove it with minimal invasion to the patient's body. To that end the system 10 basically comprises a minimal access surgical probe assembly 20 and an associated analyzer 22. The probe assembly is coupled to the analyzer by a cable 24 for detecting radiation emanating from the hidden source in a patient, e.g., a sentinel lymph node 12 (FIG. 2) tagged with the radiopharmaceutical, to localize that node, whereupon securement means (to be described later) in the probe can be operated to engage or otherwise ensnare the node so that it can be removed by the probe from the being's body for analysis.

The probe assembly 20 may be constructed so that it is an integrated instrument, e.g., the radiation detector and associated components and the securement means for ensnaring the node forming a single unit. Alternatively, and as shown in FIGS. 2 and 3 the probe assembly 20 may comprise a conventional radiation detecting probe 20A, like that described earlier, and a separate sheath or sleeve 30 for accommodating the probe 20A. To that end the sheath 30 has a central passageway 32 extending through it into which the probe 20A can be located. The sidewall of the sheath includes the heretofore mentioned tissue securement means. The sheath 30 may be constructed so that it is disposable, whereas the radiation detecting probe 20A is reusable. A detachable, side shield (not shown) in the form of a sleeve of radiation blocking material, may be located on the distal end of the probe assembly for use in high background radiation applications, e.g., when the sentinel node is close to the injection site).

In either case the probe assembly of this invention accomplishes its task by minimal invasive percutaneous penetration into the patient's body at the suspected situs of the lymph node, while the analyzer monitors the radiation picked up by the probe. By monitoring the radiation detected from the radiopharmaceutically-tagged tissue (e.g., gamma radiation, X radiation and/or annihilation radiation) and which is within the probe's solid angle of acceptance 14, the analyzer provides signals to the user to guide him/her so that the probe can be moved (by grasping its proximal end or handle 34) from the position of FIG. 2 to the position of FIG. 3 wherein its distal end 36 is located immediately adjacent the lymph node 12. At this point the tissue securement means (to be described hereafter) can be operated to ensnare the lymph node 12.

In the embodiment shown herein the securement means comprise three extendable, elongated piercing members or wires 38, 40, and 42. Each member is located within a longitudinally extending passageway 44 in the wall of the sheath 30. The members 38, 40, and 42 are arranged to be normally held in a retracted position within the sheath, so that their distal ends 46 are covered as shown in FIG. 2. This enables the probe assembly 20, i.e., the sheath 30 having the probe 20A therein, to be readily inserted either percutaneously or through a surgical incision to an internal situs, e.g., interstitial tissue, in which the distal end 36 of the probe assembly is located adjacent the radioactively tagged tissue 12, without interference caused by the extending members 38, 30 and 42. The probe can be moved or manipulated while the operator monitors the output of the analyzer 22 in order to locate the distal end of the assembly immediately adjacent the tagged tissue. At this time the extending members 38, 40 and 42 can be operated by means (not shown) to cause their distal ends 46 to extend out, e.g., 5–10 mm, of their respective passageways 44.

In accordance with a preferred aspect of this invention the extendable members 38, 40 and 42 are arranged so that, when extended, their distal ends 46 extend inward at an acute angle, e.g., 30–60 degrees, to the central longitudinal axis of the probe assembly 20 and intersect each other as shown in FIGS. 3 and 4. This action causes the members 38, 40 and 42 to pierce into the tagged tissue, if the tagged tissue is sufficiently large (e.g., 3–4 mm or greater in diameter) and thereby "lock" it in place. If the tagged tissue is smaller, the intersecting extendable members 38, 40 and 42 will not pierce the tissue but will otherwise surround it, as shown in FIG. 5. In any case, the probe assembly 20 can then be retracted or withdrawn from the being's body, carrying the tagged tissue 12 with it.

In accordance with one aspect of this invention the sheath may include means to direct the distal ends 46 of the extending members 38, 40 and 42 at an acute angle inward, or those members may be formed so that they automatically assume that orientation when they are extended out of their respective passageways 44 in the sheath 30. Moreover, means (not shown) may be provided to adjust the angle at which the members 38, 40 and 42 extend outward from the sheath.

If additional means are deemed necessary to ensure that the tagged tissue 12 is either trapped between the extending members 38, 40 and 42 and the distal end 36 of the probe assembly 20 (as shown in FIG. 5), or is pierced and ensnared (as shown in FIGS. 3 and 4) so that it does not fall off of the probe assembly during the retrieval process, additional holding means (not shown) may be provided. That means may consist of a "purse string" coupled to the extending members 38, 40 and 42 to secure them together and to the ensnared tissue. Moreover, the extending members may include means, e.g., barbs, to ensure that the tissue once grabbed or pierced does not fall off. Such barbs may be annular or longitudinal or combinations of both.

The passageways 44 in the sheath can be used to provide various other functions for the probe assembly. For example suction, from means (not shown), can be used by the probe assembly 20 to aid in holding the tagged tissue 12 in place on the distal end 36 of the probe assembly 20. The suction means can also be used to remove blood or other fluid from the operative situs.

Energy application means, e.g., a unipolar or bipolar diathermy unit, may be provided to extend out of the sheath 30 in the probe assembly 20. For example, one of the wires 38, 40 or 42 can be a unipolar diathermy wire to be extended into the tagged tissue, if desired. If bipolar diathermy is desired, two of the wires 38, 40 or 42 may be used to provide it.

Any of the passageways 44 in the sheath 30 may be used to deliver any desired material, including biologically active materials, for any desired purpose. For example, any passageway 44 can be used to deliver some flowable material to the situs of the tagged tissue to prevent the migration of cells, e.g, cancer cells, therefrom or to kill such cells.

In order to expedite the tissue localization process the probe assembly may include collimation means, e.g., a snap-on collimator (not shown), an adjustable collimator, (not shown) etc., to establish or adjust the solid angle of acceptance 14 of radioactivity by the probe assembly 20.

While the system 10 may be used without an analyzer 22 constructed in accordance with the teachings of our aforementioned copending patent application Ser. No. 08/430,589, it is preferable to use such an analyzer. In this regard the analyzer can measure the characteristic x-ray photons and full energy gamma ray photons received by the probe's sensor to determine if the ratio of the characteristic x-ray photons to the full energy gamma ray photons is appropriate for the particular radiopharmaceutical used to tag the tissue, i.e., corresponds to the natural abundance of the characteristic x-rays and full energy gamma rays for that radiopharmaceutical. If the ratio is appropriate that fact enables the operator to accurately determine the near field location of the radioactively tagged tumor since there could not be any far field source of radiation which could interfere with the precise location of the tumor (a source of far field radiation would result in an improper ratio of characteristic x-rays to full energy gamma rays). Conversely, an inappropriate ratio, e.g., a reading of significantly more full energy gamma-ray photons than characteristic x-ray photons, will indicate that the source of radiation is far field. Thus, the probe should be moved to a new position, until an appropriate ratio of characteristic x-ray photons to full energy gamma ray photons is detected.

As should be appreciated by those skilled in the art, the "sentinel node" procedure, which is the accepted modality of treatment for melanoma, and which will likely be the accepted modality of treatment for breast cancer can be effected percutaneously using the subject invention, instead of through conventional cut-down or open surgery, e.g., lumpectomy, as is the case at present. Moreover, the subject invention has particular utility for prostate cancer treatment, wherein the prostate containing the primary tumor is injected with a radiocolloid and any draining lymph nodes exhibiting radioactivity (sentinel lymph nodes) can be removed with minimum invasion to the patient. Similarly, lymph nodes identified by radiolabelled monoclonal antibodies and peptides can be detected and excised with minimum trauma.

The probe assembly 20 of this invention enables one to pierce, and snare or surround, apply suction to, suture or staple selected tagged tissue (e.g., a sentinel lymph node) and thus attach the tagged tissue to the probe tip in order to allow withdrawal of it as the probe is withdrawn. In the embodiment disclosed above the extending members or wires 38, 40 and 42 may be spring steel which are preformed to converge from a straight channel, alternatively they may be straight wires directed by angle channels, or other means in the sheath, or any combination thereof. The extending members may be tubular sections instead of solid wires (for reasons to be discussed later). In any case, the extending members can be adjusted during the operation to vary their angle of attack relative to the energy detecting probe's nose (distal end). A simple adjustment mechanism, such as a purse string attached to the tips of the extending elements can act against the intrinsic springiness or bias of the material making up those elements or can act against the applied force of the portion of the sheath causing the tips to be angled, in order to adjust the angle of attack. The angle can be adjusted from 30 to 60 degrees, in order to pierce and/or entrap and/or apply suction to the smallest lymph nodes. Additionally, at a given angle of attack, the tips of the three extending members can be advanced relative to the probe's tip to better accommodate very large lymph nodes or other tissue chunks. Moreover, at a given angle of attack, the tips of the three extending members can be retracted relative to the probe's tip to better accommodate very small lymph nodes, or other tissue chunks. Additionally, the probe 20A could be retracted relative to the sheath 30, and hence the tips of the extending members or wires 38, 40 and 42, to provide clearance for repositioning the angle of attack and so that they meet closer to the horizontal. As mentioned above, the extending members or wires can include barbs, like "fishhook barbs" and can be from about 0.1 to 3 mm long, designed to spread in response to tissue movement away from the probe's tip.

While the probe is shown with three extending members which are simultaneously advanced into or around the tissue in front of the probe tip the probe can make use of more or less members, as the case may be. In any case the probe can be used under external ultrasound guidance to accurately pierce, snare or surround, apply suction to the selected tagged tissue, while avoiding damage to adjacent blood vessels, nerves, peritoneum, pleura, and other important normal biological structures.

As mentioned earlier, it is also contemplated that the extending members, 38, 40 and 42, instead of being solid wires, can be hollow hypodermic tubing, capable of injecting appropriate substances into the lymph nodes or other tagged tissues to kill tumor cells, or to prevent the spread or seeding of tumor cells, or to initiate and propagate localized blood clotting, or for instilling other local/regional pharmacological agents. Moreover, extending members in the form of hollow tubes enable the application of suction therethrough as an additional attachment mechanism to the lymph node or other tagged tissue. Further still, the suction can be used to remove blood and/or excess fluids. As noted earlier, the channels or passageways 44 in which the extendable wires 38, 40 and 42 are located, can themselves serve as the channels for powerful suction attachment of the lymph node and other tissues. Moreover, these channels or passageways are suitable for injecting any appropriate substance into or around the lymph node or other tissues to kill tumor cells, or to prevent the spread or seeding of tumor cells, or to initiate and propagate localized blood clotting, or for instilling other local/regional pharmacological therapy, or for irrigation and suction of blood and or excess instilled fluids. Moreover, the passageways in which the extending solid wires are located, or the alternative embodiment of tubular wires, or both, can serve as means for installation of fluid solutions for other associated diagnostic and therapeutic purposes.

When the tagged node is ensnared by the probe assembly 20 it can be teased out of surrounding tissue by gentle pressure, under external ultrasound visualization, if desired. Thus, the minimally invasive radiation sensing tissue snaring probe of the invention is particularly suited to locate and retrieve sentinel nodes associated with any solid tumor, such as prostate, breast, lung, colon, rectal, and others. Scarring and trauma is thus minimized. Moreover, trauma-related-release of local growth factors, including platelet derived growth factors, which can lead to tumor reoccurrence, is also minimized.

The probe can be constructed so that it is any desired size. For example, it may be 5 to 16 mm in outside diameter, with a total length of about 9–18 inches (228.6 mm–457.2 mm). Specifically, it may be of an outside diameter of 9.5 mm for easy percutaneous introduction into the suspected site via a conventional 10 mm trocar. The distal end or nose of the probe may be configured to accept a snap on collimator, which may have approximately one millimeter channels bored into the walls, or cast as longitudinal channels or grooves on or within the inner wall of the snap on-collimator. The snap-on collimator may be made of Bismuth alloys or other low-toxicity, low-melting point, easily cast metals, or non-toxic radiation shielding composites, such as Barium filled epoxies.

An additional embodiment may consist of a 5 to 10 mm outside diameter straight probe 20A. An 8 mm version may be ensheathed in a closely fitting disposable plastic, sterile sheath 8.2 mm in inside diameter and 10 mm in outside diameter and including the tissue attachment means, i.e. the extending wires 38, 40 and 42. The optional outer sheathing cylinder 48 (FIG. 2) may be of 10.2 mm inside diameter and 12 mm outside diameter so it can be used to serve as an additional side shielding for the probe assembly 20 during the process of localizing or finding the tagged tissue or node. Alternatively, the sheathing cylinder 48 may be mounted on the probe 20A itself. Moreover, the sheath 48 may be slidable on whatever component it is mounted. The outer sheath 30, i.e., the portion which houses the extending wires 38, 40 and 42, can be made only about 25 mm long and may be constructed of any ionizing radiation shielding material. In use, that sheath may simply be slid back along the longitudinal axis of the probe 20A as the probe penetrates the skin and subcutaneous tissues. That sheath may also simply be slipped off the front of the probe 20A after percutaneous localization of the radioactive node or other tissue, prior to skin penetration. The outer sheath 30 should allow the probe to detect signal from the node as low as 2.5 counts per second, despite noise from the nearby injection site, which may be emitting as much as 37,000 counts per second. Positioning of the leading or distal edge 36 of the outer sheath 30 can be flush with the probe 20A tip or forward of the probe tip, as desired.

The radiation shielding necessary to initially find the node adjacent to a very high background count is substantially greater than the shielding required to track the dissection of that localized node. The sheath 30 or the optional outer sheath (not shown) may be about 10 half value layers thick (1.9 mm for Tungsten 95% alloy at 140 keV) and the intrinsic probe walls shielding may be about 7 half value layers thick (1.33 mm for Tungsten 95% alloy at 140 keV). Thus, the reusable probe sheath may be as little as 5 millimeters in diameter (2.66 mm thick with a wall, 2.0 mm diameter radiation detector) while still having 99% exclusion of side incident protons.

The detector may be a rod of Cesium Iodide or of Gadolinium Orthosilicate, either of which is only doped with a scintillation activator at one end to produce an active region approximately 3 mm long, in a rod that may be 100 mm long. In this arrangement, there is no light loss between the scintillation detector portion of the rod and the light pipe, as there were would if there were separate joined pieces of scintillator and light pipe. The sides and one end of the rod may be coated with reflective material, such as a thin-layer-deposition of gold, silver, platinum, etc., or a thin-layer-deposition of Teflon reflective material. Thus, a highly efficient, very small diameter intrastitial or endoscopic probe may be constructed, wherein the light pipe material provides backshielding against injection site radioactivity.

The diathermy capability of the probe assembly as described earlier provides the option of cutting attached tissues or of coagulating bleeding vessels. For unipolar or monopolar diathermy coagulation, only one of the extending wires is advanced from the probe tip and the probe is rotated. For bipolar diathermy, two wires are partially advanced, leaving a tissue gap between them. Monopolar diathermy can be accomplished with one or more wires, as desired.

A sterile disposable accessory (not shown) ensheathing the probe can be combined with a sterile disposable probe power cord, or can be combined with a sterile disposable power cord sheath. Alternatively, a self contained probe can be placed inside a "Ziploc" sterile disposable accessory container.

It is also contemplated that the probe itself can be self contained, that is the probe includes radiation signal analyzing circuitry and a self-contained power source, e.g., one or more batteries, for effecting tagged tissue localization and retrieval.

Figures 6, 7:
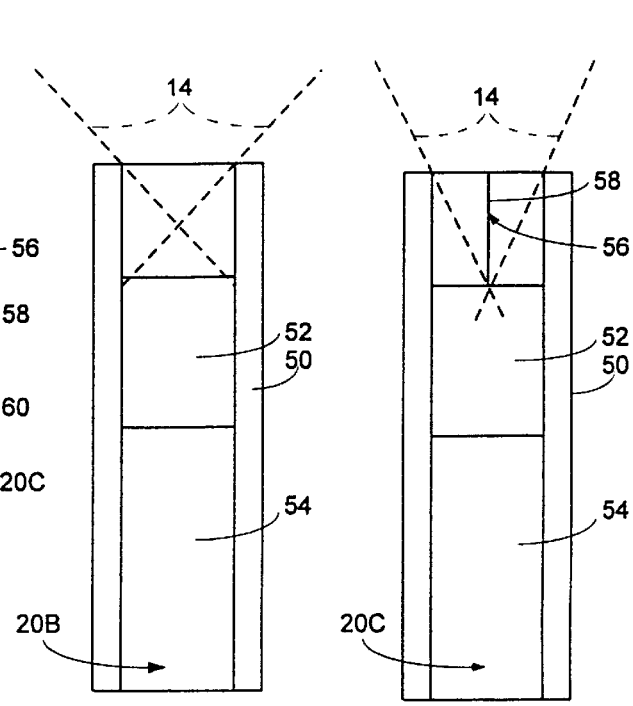
FIG. 6 is a longitudinal sectional view of a probe incorporating a single-hole collimator which can be used as part of the probe assembly of the subject invention.
FIG. 7 is a longitudinal sectional view of a probe incorporating a dividable single-hole collimator which can be used as part of the probe assembly of the subject invention.

In FIG. 6 there is shown a probe incorporating a single-hole collimator which can be used as part of the probe assembly 20 of the subject invention. That probe is designated by the reference number 20B and basically comprises a cylindrical sidewall 50 formed of a radiation shielding material. A scintillation crystal 52 is located within the interior of the sidewall a short distance proximally of the distal end of the sidewall, so that the sidewall serves as a single hole collimator establishing the probe's solid angle of acceptance 14 for producing a valid signal. A photomultiplier or a photodiode 54 is located distally of the crystal 52 to receive the light flashes produced by the crystal 52 from radiation impinging on it within the probe's solid angle of acceptance.

Other collimation can be used to reduce or narrow the solid angle of acceptance of the probe of this invention. In fact, such collimation may be adjustable. To that end in FIGS. 7–9 there is shown a probe incorporating a dividable single-hole collimator which can be used as part of the probe assembly of the subject invention. That probe is designated by the reference number 20C and is identical in construction to probe 20B, except that it includes an operable collimation assembly 56 (to be described hereinafter). In the interests of brevity the common components of probes 20B and 20C will be given the same reference numbers and their construction and operation will not be reiterated. The operable collimation assembly 56 is arranged to be selectively operated in either a "single hole mode," shown in FIG. 9, or in a "divided hole mode," shown in FIGS. 7 and 8. In the single hole mode the probe 20C provides a field of view or solid angle of acceptance 14 similar to the probe 20B and which is shown in FIG. 6. In the divided hole mode, the probe 20C provides a narrower solid angle of acceptance 14 like that shown in FIG. 7. To accomplish that end the collimator assembly 56 is made up of plural, e.g., three, hinged pivotable wall members or septa 58. Each of the septa is a planar member made up of a radiation resistant material, e.g., lead, or tungsten or platinum-irridium, and which is hingedly connected at 60 to the inside surface of the cylindrical sleeve 50 immediately distally of the distal end of the scintillation crystal 52 to create two or more channels 62 (in the embodiment shown herein three such channels, to be described hereinafter, are formed as shown in FIG. 8).

Figure 9:
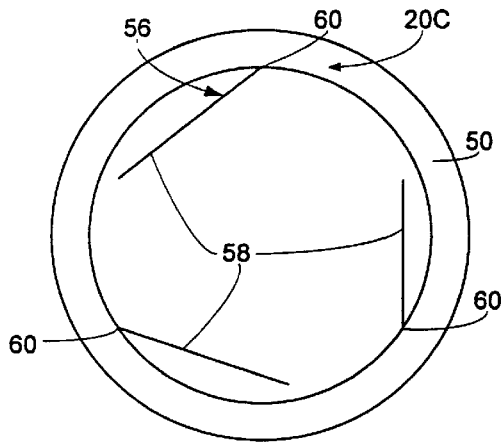
FIG. 9 is an end view of the divided single-hole collimator shown n its divided state.

When the probe 20C is in the single hole mode the septa 58 are pivoted back to the position shown in FIG. 9, whereupon virtually the entire interior space within the cylindrical sidewall 50 distally of the crystal 52 is available to have radiation pass therethrough within the solid angle of acceptance 14 shown in FIG. 6. In the divided hole mode the septa 58 are pivoted to the operative or closed position shown in FIG. 8 wherein each free edge (i.e., the edge opposite the edge which is pivotally connected to the cylindrical sidewall) engages the respective free edges of the other septa to effectively divide the interior of the cylinder distally of the crystal into three identically sized pie-shaped sectors or channels 62. Each of these channels forms what may be considered its own single hole collimator, so that the combined effect of these three "single hole collimators" is a combined (divided) collimator, whose combined solid angle of acceptance 14 is substantially narrower than when the probe 20C is in the single hole mode as can be seen in FIG. 7.

Figure 10:
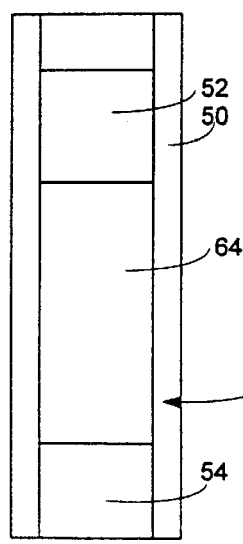
FIG. 10 is a longitudinal sectional view of a probe incorporating a back shielding light pipe which can be used as part of the probe assembly of the subject invention.

In FIG. 10 there is shown a probe 20D incorporating radiation back shielding component which can be used as part of the probe assembly of the subject invention. The probe 20D is similar to probe 20B described above, except for the inclusion of a backshielding lightpipe 64 (to be described hereinafter). In the interest of brevity the common features of probes 20B and 20D will be given the same reference numbers. The backshielding lightpipe 64 is formed of any suitable optically transparent but radiation resistant material, e.g., radiopaque, material. As is known, scintillation crystals typically require a dopant to scintillate in response to ionizing radiation. Undoped Gadolineum Orthosilicate or undoped Bismuth Germinate or undoped Cesium Iodide or even a lead-glass lightpipe can be used to form the backshielding lightpipe 64. Thus, with the probe 20D all scintillation events detected by the probe's crystal 52 will be those arising from the front (distal end) of the probe. Ideally the backshielding lightpipe 64 has the same optical index of refraction as the scintillation crystal 52. The simplest way to achieve this goal is to use an undoped light pipe that is made of the same material as the scintillation crystal, with an index of refraction matched optical coupling gel or adhesive (not shown). Alternatively, lead-glass can also be fabricated with various indices of refraction specifications to approximate the index of refraction of the scintillation crystal 52. An optical coupling compound with an index of refraction half way between the crystal and the lightpipe can be used to maximize optical performance of the two part assembly. An alternative, and more elegant approach, is to create a combined scintillator-lightpipe, starting with an undoped crystal lightpipe, that is without the dopant which allows the scintillation crystal to emit flashes of light. In particular, a rod of undoped scintillation crystal, such as undoped Gadolineum Orthosilicate or undoped Bismuth Germinate, or undoped Cesium Iodide is used, but only one end of the rod is doped with the necessary scintillation dopant to form a scintillation crystal at that end, while the undoped portion forms the lightpipe. As will be appreciated, this arrangement will not have an optical joint between the crystal and lightpipe. The deposition of dopants may be accomplished by any implantation technology appropriate to the crystal depth to be treated. Elimination of the optical joint should allow higher spectral resolution and higher sensitivity within the photopeak due to the elimination of optical interface losses.

Without further elaboration the foregoing will so fully illustrate my invention that others may, by applying current or future knowledge, adopt the same for use under various conditions of service.

What is claimed is:

1. A hand-holdable instrument for minimally invasive percutaneous introduction within the body of a living being for detecting radiation emanating from radioactively tagged tissue within the being's body, said instrument comprising a probe and at least one, thin, elongated extendable member, said probe including a radiation detector arranged to determine the location of the radioactively tagged tissue from within the body of the being to enable the instrument to be moved so that said radiation detector is adjacent to the radioactively tagged tissue, said at least one extendable member being located adjacent said radiation detector and arranged to be extended out of said probe to ensnare the radioactively tagged tissue and to secure it as a unit to said probe, whereupon said instrument may be moved with respect to the being's body to remove the radioactively tagged tissue as a unit from the being's body so as to cause minimal disruption of the tagged tissue.

2. The instrument of claim 1 wherein said instrument includes plural, thin, elongated extendable members to pierce into the radioactively tagged tissue from plural directions to ensnare the radioactively tagged tissue.

3. The instrument of claim 1 wherein said probe comprises a body member including a radiation blocking material, said radiation detector being located within said body member, said body member having a distal end portion and a proximal end portion, said proximal end portion being arranged to be held in the hand of a user, said distal end portion being arranged to be directed toward a suspected location of the radioactively tagged tissue, said at least one extendable member being extendable from said distal end portion.

4. The instrument of claim 1 wherein said radiation detector comprises a scintillation crystal.

5. The instrument of claim 4 wherein said radiation detector has a solid angle of acceptance of radiation and wherein said instrument comprises a collimator for establishing the solid angle of acceptance of said radiation detector to radiation emanating from said radioactively tagged tissue.

6. The instrument of claim 5 wherein said radiation detector comprises a crystal and where said instrument additionally comprises a backshielding member located proximally of said crystal to block radiation from the proximal direction to said crystal.

7. The instrument of claim 1 including a suction passageway.

8. The instrument of claim 1 wherein said probe comprises a tubular sheath, said radiation detector being arranged to be releasably located within said tubular sheath, said tubular sheath including said at least one extendable member.

9. The instrument of claim 8 wherein said tubular sheath comprises a disposable material.

10. The instrument of claim 1 wherein said radiation detector has a solid angle of acceptance of radiation and wherein said instrument comprises a collimator, said collimator establishing the solid angle of acceptance of the radiation detector to the radiation emanating from the radioactively tagged tissue.

11. The instrument of claim 10 wherein said collimator is adjustable to adjust said solid angle of acceptance.

12. The instrument of claim 11 wherein said adjustable collimator includes at least one movable member arranged to be moved from a first position establishing a first, solid angle of acceptance of said radiation detector, and to a second position establishing a second and narrower solid angle of acceptance of said radiation detector.

13. The instrument of claim 1 additionally comprising diathermy means for applying energy to the radioactively tagged tissue.

14. The instrument of claim 1 wherein said at least one extendable member is barbed.

15. The instrument of claim 1 wherein said probe has a longitudinal axis and wherein said at least one extendable member is arranged to be extended at an acute angle to said longitudinal axis.

16. The instrument of claim 15 wherein said at least one extendable number is adjustable and is arranged to be extended at an adjustable angle to said longitudinal axis.

17. The instrument of claim 1 additionally comprising means for introducing a biologically active material adjacent the radioactively tagged tissue.

18. The instrument of claim 1 wherein said radiation detector comprises a crystal and where said instrument additionally comprises a backshielding member located proximally of said crystal to block radiation from the proximal direction to said crystal.

19. The instrument of claim 18 wherein said backshielding member comprises a lightpipe.

20. The instrument of claim 19 wherein said lightpipe comprises a material selected from the group consisting of undoped Gadolineum Orthosilicate, undoped Bismuth Germinate, undoped Cesium Iodide, and lead-glass.

21. The instrument of claim 20 additionally comprising an optical interface and wherein said lightpipe is connected to said crystal via said optical interface, said optical interface comprising either an optical coupling gel or adhesive.

22. The instrument of claim 20 wherein said crystal and said lightpipe are an integral unit comprising a material selected from the group consisting of undoped Gadolineum Orthosilicate, undoped Bismuth Germinate, undoped Cesium Iodide, and wherein said crystal comprises a scintillation doped portion of said material.

23. A method of removing radioactively tagged tissue within a living being's body, the radioactively tagged tissue having radiation emanating therefrom, said method comprising the steps of:
   (a) providing a probe device having a radiation detector and at least one, thin elongated extendable member,
   (b) minimally invasively introducing said probe device within the body of the being for detecting radiation emanating from the radioactively tagged tissue within the being's body by said radiation detector,
   (c) positioning the probe device so that said radiation detector is located adjacent the radioactively tagged tissue,
   (d) operating said probe device to cause said at least one extendable member to ensnare the radioactively tagged tissue, and
   (e) removing the probe and the snared tissue as a unit from the being's body so as to cause minimal disruption of the tagged tissue.

24. The method of claim 23 wherein said radioactively tagged tissue is located within the a cavity, duct, lumen or vessel in the body of the being, and wherein said probe device is introduced with minimal invasion of the being's body.

25. The method of claim 23 wherein said radioactively tagged tissue is located within an organ in the body of the being, and wherein said probe device is introduced with minimal invasion of the being's body.

26. The method of claim 23 wherein said radioactively tagged tissue is located interstitially, and wherein said probe device is introduced with minimal invasion of the being's body.

27. The method of claim 23 wherein said radioactively tagged tissue comprises a lymph node.

28. The method of claim 23 additionally comprising the step of providing suction adjacent said radioactively tagged tissue to facilitate the holding of said tissue.

29. The method of claim 23 additionally comprising the step of providing suction adjacent said radioactively tagged tissue to remove blood and/or other fluids.

30. The method of claim 23 additionally comprising the step of introducing a flowable material adjacent the radioactively tagged tissue to minimize the migration of cells therefrom.

31. The method of claim 23 additionally comprising the step of introducing a biologically active material adjacent the radioactively tagged tissue.

32. The method of claim 23 wherein said probe device includes a body portion, and wherein said at least one extendable member is arranged to be held in a retracted position with respect to said body portion of said probe device, and wherein said method comprises extending said at least one extendable member from said retracted position to an extended position to pierce and snare the radioactively tagged tissue.

33. The method of claim 32 additionally comprising the step of providing energy to the radioactively tagged tissue.

34. The method of claim 33 wherein said energy is applied by diathermy means forming a portion of said probe device.

35. A hand-holdable instrument for minimally invasive percutaneous introduction within the body of a living being for detecting radiation emanating from a lymph node tagged with a radioactive agent and for efficiently removing that lymph node from the body of the being, said instrument comprising a probe and at least one, thin, elongated extendable member, said probe including a radiation detector arranged to determine the location of the radioactively tagged lymph node from within the body of the being to enable the instrument to be moved so that said radiation detector is adjacent to the radioactively tagged lymph node, said at least one extendable member being constructed and arranged to be extended out of said probe to engage into the radioactively tagged lymph node with minimal disturbance of the tissue of the lymph node to ensnare the lymph node, whereupon said instrument may be moved with respect to the being's body to efficaciously remove the radioactively tagged lymph node as a unit from the being's body so as to cause minimal disruption of the tagged lymph node.

36. The instrument of claim 35 wherein said instrument includes plural, thin, elongated extendable members to pierce into the radioactively tagged lymph node from plural directions to ensnare it.

37. The instrument of claim 35 wherein said probe comprises a body member including a radiation blocking material, said radiation detector being located within said body member, said body member having a distal end portion and a proximal end portion, said proximal end portion being arranged to be held in the hand of a user, said distal end portion being arranged to be directed toward a suspected location of the radioactively tagged lymph node, said at least one extendable member being extendable from said distal end portion.

38. The instrument of claim 35 wherein said radiation detector comprises a scintillation crystal.

39. The instrument of claim 38 wherein said radiation detector has a solid angle of acceptance of radiation and wherein said device comprises a collimator for establishing the solid angle of acceptance of said radiation detector to radiation emanating from said radioactively tagged lymph node.

40. The instrument of claim 39 wherein said radiation detector comprises a crystal and where said instrument additionally comprises a backshielding member located proximally of said crystal to block radiation from the proximal direction to said crystal.

41. The instrument of claim 35 including a suction passageway.

42. The instrument of claim 35 wherein said probe comprises a tubular sheath, said radiation detector being arranged to be releasably located within said tubular sheath, said tubular sheath including said at least one extendable member.

43. The instrument of claim 42 wherein said tubular sheath comprises a disposable material.

44. The instrument of claim 35 additionally comprising diathermy means for applying energy to the radioactively tagged tissue.

45. The instrument of claim 35 wherein said at least one extendable member is barbed.

46. The instrument of claim 35 wherein said probe has a longitudinal axis and wherein said at least one extendable member is arranged to be extended at an acute angle to said longitudinal axis.

47. The instrument of claim 46 wherein said at least one extendable number is adjustable and is arranged to be extended at an adjustable angle to said longitudinal axis.

48. The instrument of claim 35 additionally comprising means for introducing a biologically active material adjacent the radioactively tagged lymph node.

49. The instrument of claim 35 wherein said radiation detector has a solid angle of acceptance of radiation and wherein said instrument comprises a collimator for establishing the solid angle of acceptance of said radiation detector to radiation emanating from the radioactively tagged lymph node.

50. The instrument of claim 49 wherein said collimator is adjustable to adjust said solid angle of acceptance.

51. The instrument of claim 50 wherein said adjustable collimator includes at least one movable member arranged to be moved from a first position establishing a first, solid angle of acceptance of said radiation detector, to a second position establishing a second and narrower solid angle of acceptance of said radiation detector.

52. The instrument of claim 35 wherein said radiation detector comprises a crystal and where said instrument additionally comprises a backshielding member located proximally of said crystal to block radiation from the proximal direction to said crystal.

53. The instrument of claim 52 wherein said backshielding member comprises a lightpipe.

54. The instrument of claim 53 wherein said lightpipe comprises a material selected from the group consisting of undoped Gadolineum Orthosilicate, undoped Bismuth Germinate, undoped Cesium Iodide, and lead-glass.

55. The instrument of claim 54 additionally comprising an optical interface and wherein said lightpipe is connected to said crystal via said optical interface, said optical interface comprising either an optical coupling gel or adhesive.

56. The instrument of claim 54 wherein said crystal and said lightpipe are an integral unit comprising a material selected from the group consisting of undoped Gadolineum Orthosilicate, undoped Bismuth Germinate, undoped Cesium Iodide, and wherein said crystal comprises a scintillation doped portion of said material.

57. A method of removing a lymph node tagged with a radioactive agent from the body of a living being, the lymph node having radiation emanating therefrom, said method comprising the steps of:
  (a) providing a probe device having a radiation detector and at least one, thin elongated extendable member,
  (b) introducing said device within the body of the being for detecting radiation emanating from said radioactively tagged lymph node by said radiation detector,
  (c) positioning said probe device so that said radiation detector is located adjacent the radioactively tagged lymph node,
  (d) operating said probe device to cause said at least one extendable member to ensnare the radioactively tagged lymph node, and
  (e) removing said probe device and the snared lymph node as a unit from the being's body so as to cause minimal disruption of the tagged lymph node.

58. The method of claim 57 additionally comprising the step of providing suction adjacent said radioactively tagged lymph node.

59. The method of claim 57 additionally comprising the step of introducing a flowable material adjacent the radioactively tagged lymph node.

60. The method of claim 57 additionally comprising the step of introducing a biologically active material adjacent the radioactively tagged lymph node.

61. The method of claim 57 wherein said probe device includes a body portion, and wherein said at least one extendable member is arranged to be held in a retracted position with respect to said body portion of said probe device, and wherein said method comprises extending said at least one extendable member from said retracted position to an extended position to pierce and snare the radioactively tagged lymph node.

62. The method of claim 61 wherein said extendable member is extended to pierce into the radioactively tagged lymph node.

63. The method of claim 62 additionally comprising the step of providing energy to the radioactively tagged lymph node.

64. The method of claim 63 wherein said energy is applied by diathermy means forming a portion of said probe device.

65. The method of claim 57 wherein said lymph node is a sentinel node.

\* \* \* \* \*